(12) United States Patent
Deanglis et al.

(10) Patent No.: US 11,666,682 B2
(45) Date of Patent: Jun. 6, 2023

(54) METHOD OF STOPPING CSF LEAKS AND APPARATUS THEREFOR

(71) Applicant: ETHICON, INC., Somerville, NJ (US)

(72) Inventors: Ashley Deanglis, Skillman, NJ (US); Salim Ghodbane, Skillman, NJ (US); Kevin Shaun Weadock, Hillsborough, NJ (US)

(73) Assignee: Ethicon, Inc., Raritan, NJ (US)

( * ) Notice: Subject to any disclaimer, the term of this patent is extended or adjusted under 35 U.S.C. 154(b) by 61 days.

(21) Appl. No.: 17/008,062

(22) Filed: Aug. 31, 2020

(65) Prior Publication Data

US 2022/0062504 A1 Mar. 3, 2022

(51) Int. Cl.
*A61L 27/36* (2006.01)
*A61L 27/22* (2006.01)

(52) U.S. Cl.
CPC ......... *A61L 27/3675* (2013.01); *A61L 27/225* (2013.01); *A61L 27/3687* (2013.01); *A61L 2400/06* (2013.01)

(58) Field of Classification Search
CPC ............... A61L 27/3675; A61L 27/225; A61L 27/3687; A61L 2400/06
See application file for complete search history.

(56) References Cited

U.S. PATENT DOCUMENTS

| | | | |
|---|---|---|---|
| 5,844,087 A | 12/1998 | Zimmerman et al. | |
| 8,500,776 B2 | 8/2013 | Ebner | |
| 8,529,941 B2 | 9/2013 | Hakimimehr et al. | |
| 9,956,311 B2 | 5/2018 | Ericson | |
| 2005/0095235 A1* | 5/2005 | Austin | |
| 2011/0182991 A1* | 7/2011 | Ilan | |
| 2018/0021555 A1 | 1/2018 | Morriss et al. | |

FOREIGN PATENT DOCUMENTS

| | | |
|---|---|---|
| JP | 2012110514 A | 6/2012 |
| WO | 2014121000 A1 | 8/2014 |

OTHER PUBLICATIONS

International Search Report for related International Application No. PCT/IB2021/057121, dated Oct. 14, 2021, 10 pages.
Iwata et al., "Effective Repair of Dural Tear Using Bioabsorbable Sheet With Fibrin Glue", Spine vol. 42, No. 18, Sep. 15, 2017, pp. 1362-1366.
Uliveri et al., "From surgery to neurosurgery: our experience on the efficacy of fleece-bound sealing (TachoSil®) for dural repair", G Chir vol. 35—n. 7/8, Jul. 1, 2014, pp. 195-198.
Yamamoto et al., "Experimental Study of Intraparenchymal Fibrinogen and Topical Thrombin to Seal Pleural Defects", Tokai J Exp Clin Med., vol. 41, No. 4, Jan. 1, 2016, pp. 185-189.

* cited by examiner

*Primary Examiner* — Alma Pipic

(57) ABSTRACT

A method and kit for stopping cerebrospinal fluid (CSF) leaks, comprising penetrating and passing through a dural tissue an applicator to access an interior dural space, injecting from the applicator a fibrinogen-containing solution into said dural space, applying a sealing member containing a fibrinogen polymerizing agent onto an exterior surface of the dural tissue, and forming a polymerized fibrinogen or polymerized fibrin clot by contacting the injected fibrinogen-containing solution and the fibrinogen polymerizing agent.

13 Claims, 1 Drawing Sheet

METHOD OF STOPPING CSF LEAKS AND APPARATUS THEREFOR

FIELD

This disclosure relates to a method for stopping leakage of cerebrospinal fluid from a dural space which may develop as a result of injury or surgery.

ENVIRONMENT

The dural mater is located between the cranium and the brain and around the spinal cord. The principal function of the dural mater is to protect the brain and spinal cord and prevent leakage of cerebrospinal fluid (CSF).

It is possible for the dural mater to become unintentionally or intentionally perforated. Unintentional perforation of the dural mater may occur from a traumatic event like an automobile accident or through accidental perforation during surgical procedures. Intentional dural mater perforation can occur when performing certain surgical procedures, such as to provide access to the brain, spinal cord, or other structures within the central nervous system.

In both of these situations, it is important to quickly and reliably seal the dural mater to minimize the loss of cerebrospinal fluid as the cerebrospinal fluid plays a critical role in supporting the brain in the cranium. Additionally, the body has a limited ability to produce cerebrospinal fluid in order to replace the cerebrospinal fluid that is lost. If the loss of cerebrospinal fluid is not quickly stopped, the patient may experience serious health complications and possibly death.

Previous efforts at sealing CSF leaks have generally been directed to placing a hemostatic dressing or other hemostatic sealant over the location of the leak(s). However, the efficacy of such methods is dependent upon identification of the location of the leak site(s), which can be difficult. Once the location of the leak is identified, it is necessary to have adequate access to the site(s) for application of a dressing or sealant, which may be challenging due to the anatomical structures surrounding the brain and spinal cord.

SUMMARY

Provided is a method for stopping cerebrospinal fluid (CSF) leaks, comprising penetrating and passing through a dural tissue an applicator to access an interior dural space, injecting from the applicator a fibrinogen-containing solution into said dural space, applying a sealing member containing a fibrinogen polymerizing agent onto an exterior surface of the dural tissue, and forming a polymerized fibrinogen or polymerized fibrin clot by contacting the injected fibrinogen-containing solution and the fibrinogen polymerizing agent.

In one form, the fibrinogen polymerizing agent can be selected from thrombin, thrombin with Factor XIII and thrombin-like enzymes, such as those present in snake venom.

In another form, the fibrinogen polymerizing agent can be a fibrinogen binding peptide or fibrinogen binding precursor peptide.

In yet another form, the sealing member can be in the form of a patch, a powder, a paste, a gelatin, a spray, a foam, or a liquid.

Advantageously, the fibrinogen can be injected into the dural space prior to applying the sealing member, or the sealing member can be applied prior to injecting the fibrinogen into the dural space. In some forms, the fibrinogen can be injected into the dural space in the vicinity of a defect in the dural tissue.

In one form, the dural tissue can be located below a patient's skull.

In another form, the dural tissue can be located in a patient's lumbar portion of the spinal cord.

In yet another form, the dural tissue can be located between a patient's skull and lumbar portion of the spinal cord.

Advantageously, the amount of fibrinogen injected into said dural space can be sufficient to raise a 15 mL local volume concentration of fibrinogen in CSF fluid to at least about 0.75 mg/mL, such as from about 0.75 mg/mL to about 3 mg/m L.

In one form, the fibrinogen containing solution can be free of thrombin.

Also presented herein is a kit for plugging a CSF leak site, comprising a syringe containing a fibrinogen-containing solution and a patch slidably disposed on a needle of said syringe, said patch containing a fibrinogen polymerizing agent.

In one form, the fibrinogen polymerizing agent can be selected from thrombin, thrombin with Factor XIII and thrombin-like enzymes, such as those present in snake venom.

In another form, the fibrinogen polymerizing agent can be a fibrinogen binding peptide or fibrinogen binding precursor peptide.

BRIEF DESCRIPTION OF THE DRAWINGS

The present disclosure is susceptible to various modifications and alternative forms, specific exemplary implementations thereof have been shown in the drawings and are herein described in detail. It should be understood, however, that the description herein of specific exemplary implementations is not intended to limit the disclosure to the particular forms disclosed herein.

This disclosure is to cover all modifications and equivalents as defined by the appended claims. It should also be understood that the drawings are not necessarily to scale, emphasis instead being placed upon clearly illustrating principles of exemplary embodiments of the present disclosure. Moreover, certain dimensions may be exaggerated to help visually convey such principles. Further where considered appropriate, reference numerals may be repeated among the drawings to indicate corresponding or analogous elements. Moreover, two or more blocks or elements depicted as distinct or separate in the drawings may be combined into a single functional block or element. Similarly, a single block or element illustrated in the drawings may be implemented as multiple steps or by multiple elements in cooperation.

The forms disclosed herein are illustrated by way of example, and not by way of limitation, in the figures of the accompanying drawings and in which like reference numerals refer to similar elements and in which:

Figure 1:
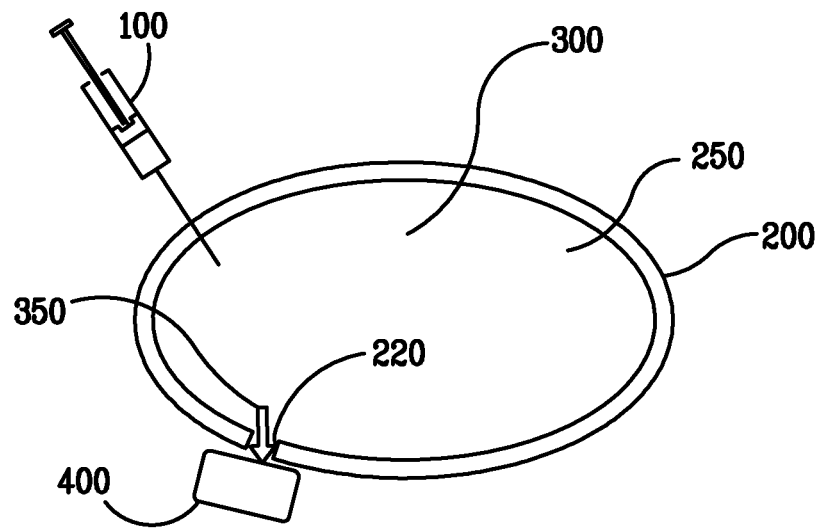
Figure 2:
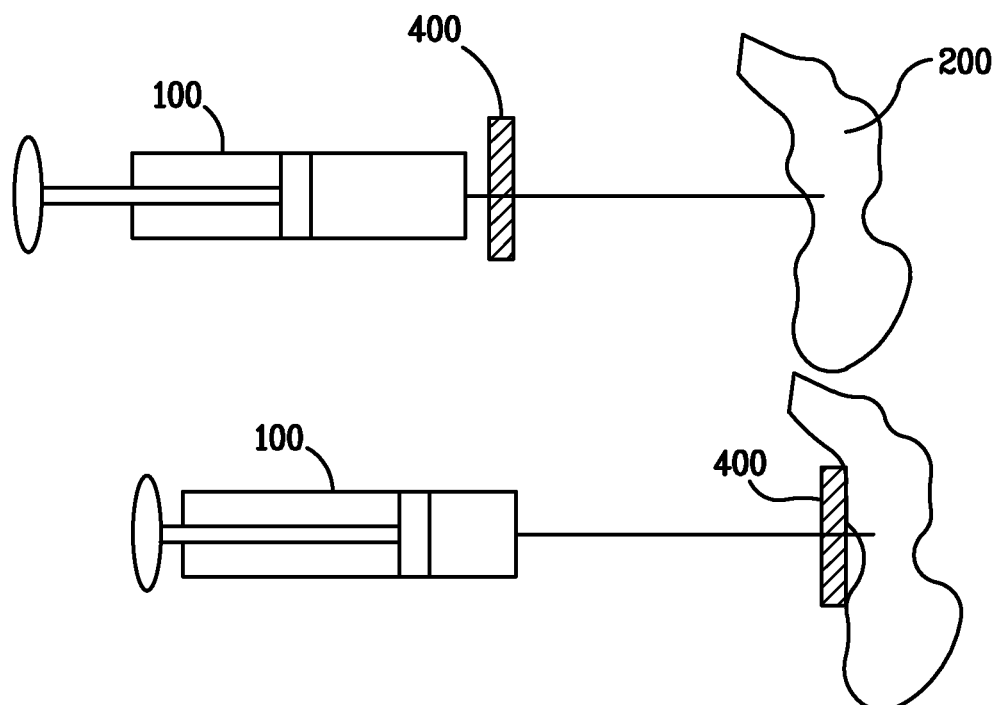

FIG. 1 presents an illustration of the method of sealing a CSF leak from a dural space, according to the present disclosure; and FIG. 2 presents a kit suitable for performing the method of FIG. 1.

DETAILED DESCRIPTION

Various aspects will now be described with reference to specific forms selected for purposes of illustration. It will be appreciated that the spirit and scope of the apparatus, system and methods disclosed herein are not limited to the selected forms. Moreover, it is to be noted that the figures provided herein are not drawn to any particular proportion or scale, and that many variations can be made to the illustrated forms.

Each of the following terms written in singular grammatical form: "a," "an," and "the," as used herein, may also refer to, and encompass, a plurality of the stated entity or object, unless otherwise specifically defined or stated herein, or, unless the context clearly dictates otherwise. For example, the phrases "a device," "an assembly," "a mechanism," "a component," and "an element," as used herein, may also refer to, and encompass, a plurality of devices, a plurality of assemblies, a plurality of mechanisms, a plurality of components, and a plurality of elements, respectively.

Each of the following terms: "includes," "including," "has," "having," "comprises," and "comprising," and, their linguistic or grammatical variants, derivatives, and/or conjugates, as used herein, means "including, but not limited to."

Throughout the illustrative description, the examples, and the appended claims, a numerical value of a parameter, feature, object, or dimension, may be stated or described in terms of a numerical range format. It is to be fully understood that the stated numerical range format is provided for illustrating implementation of the forms disclosed herein and is not to be understood or construed as inflexibly limiting the scope of the forms disclosed herein.

Moreover, for stating or describing a numerical range, the phrase "in a range of between about a first numerical value and about a second numerical value," is considered equivalent to, and means the same as, the phrase "in a range of from about a first numerical value to about a second numerical value," and, thus, the two equivalently meaning phrases may be used interchangeably.

It is to be understood that the various forms disclosed herein are not limited in their application to the details of the order or sequence, and number, of steps or procedures, and sub-steps or sub-procedures, of operation or implementation of forms of the method or to the details of type, composition, construction, arrangement, order and number of the system, system sub-units, devices, assemblies, sub-assemblies, mechanisms, structures, components, elements, and configurations, and, peripheral equipment, utilities, accessories, and materials of forms of the system, set forth in the following illustrative description, accompanying drawings, and examples, unless otherwise specifically stated herein. The apparatus, systems and methods disclosed herein can be practiced or implemented according to various other alternative forms and in various other alternative ways.

It is also to be understood that all technical and scientific words, terms, and/or phrases, used herein throughout the present disclosure have either the identical or similar meaning as commonly understood by one of ordinary skill in the art, unless otherwise specifically defined or stated herein. Phraseology, terminology, and, notation, employed herein throughout the present disclosure are for the purpose of description and should not be regarded as limiting.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a range of about 1 to about 200 should be interpreted to include not only the explicitly recited limits of 1 and about 200, but also to include individual sizes such as 2, 3, 4, etc. and sub-ranges such as 10 to 50, 20 to 100, etc. Similarly, it should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds). In the figures, like numerals denote like, or similar, structures and/or features; and each of the illustrated structures and/or features may not be discussed in detail herein with reference to the figures. Similarly, each structure and/or feature may not be explicitly labeled in the figures; and any structure and/or feature that is discussed herein with reference to the figures may be utilized with any other structure and/or feature without departing from the scope of the present disclosure.

Unlike blood leaking from blood vessels which has fibrinogen to aid in the sealing of the "blood" leak, cerebral spinal fluid (CSF) doesn't normally contain significant concentrations of fibrinogen, so there is nothing in the CSF that can polymerize at the defect site to stop the leak. CSF contains about $\frac{1}{1000}$ of fibrinogen of plasma, which amount is insufficient to promote hemostasis at a leak site in dural matter using a conventional hemostatic covering. Conventional hemostats containing thrombin or used in combination with thrombin are known, such as Surgifoam® and Surgiflo® with thrombin, Evicel® or Evarrest®, available from Johnson & Johnson, New Brunswick, N.J.

It has been discovered that CSF leaks can be stopped by injection of a fibrinogen-containing fluid through the dura into the dural space and allowing it to leak to the outside of the dura, forming fibrin outside and within the leak area channel through a reaction with thrombin in these areas and stopping the leak, thus increasing CSF fibrinogen concentration from natural CSF concentration to a higher concentration, such as up to plasma level or higher. A sealing member (patch, powder, paste, gelatin, liquid, etc.) containing thrombin or another fibrinogen cross-linking agent is applied to the site of leak, resulting in the leak site plugging by fibrin.

Referring to FIG. 1, the disclosure relates to a method for stopping CSF 300 leaks, comprising penetrating and passing through a dural tissue 200 an applicator 100, such as a syringe, to access an interior dural space 250, injecting from the applicator a fibrinogen-containing solution into said dural space 250, applying a sealing member 400 containing a fibrinogen polymerizing agent onto an exterior surface of the dural tissue, and forming a polymerized fibrinogen or polymerized fibrin clot by contacting the injected fibrinogen-containing solution and the fibrinogen polymerizing agent. As a result, a fibrinogen-containing CSF fluid 350 exits through a dural tissue defect 220 and the fibrinogen polymerizes in the presence of a fibrinogen polymerizing agent located in sealing member 400. The fibrinogen can be free of thrombin.

The fibrinogen polymerizing agent can be selected from thrombin, thrombin with Factor XIII and thrombin-like enzymes, such as those present in snake venom. The thrombin may be human-derived, recombinant, or animal-derived (bovine, porcine, salmon or other species), and includes intermediates or derivatives of thrombin, e.g. meizothrombin (which is active against fibrinogen) or degraded forms of thrombin, e.g. beta thrombin, which has reduced activity against fibrinogen.

Polymerizing agents can be derived from snake venom enzymes that have thrombin-like enzyme activity. There are many but three commonly used agents are: (1) Batroxobin from snake species *Bothrops atrox*; (2) Ancrod from snake species *Agkistrodon rhodostoma*; and (3) Venzyme from snake species *Agkistrodon contortrix*. The polymerizing agent can also include recombinant forms of these snake venom enzymes.

Alternatively, the fibrinogen polymerizing agent can be a fibrinogen binding peptide or fibrinogen binding precursor peptide, such as those described in U.S. Published Application No. 2014/0031293, incorporated herein by reference. For example, a suitable polymerizing agent can be one of the following general formula (I):

$$[\text{Peptide-CO-A-X-B-}]_n \text{ Carrier} \quad (I)$$

wherein:
"Peptide-CO" represents a fibrinogen binding peptide or fibrinogen binding precursor peptide and the main chain α-carbonyl group at the carboxy-terminal end of the peptide;
"-A-X-B-" represents the non-peptide spacer, where A is a first linker of the non-peptide spacer covalently linked directly to the main chain α-carbonyl group of the peptide, X is a spacer group, and B is a second linker of the non-peptide spacer covalently linked to the carrier; and
n is >1, and so indicates that a plurality of fibrinogen binding peptides or fibrinogen binding precursor peptides are covalently linked to the carrier.

Preferably X is a hydrophilic group, preferably a straight chain hydrophilic group, more preferably a polyethylene oxide group, suitably of formula $-(CH_2CH_2O)_x-$, where x is at least 1, 2, 4, 6, 8, 10 or 20. Preferably X is up to 50, for example, 1-50, preferably 2-24.

In one form, linker A comprises an —NH— group which forms an amide bond together with the main chain α-carbonyl group of the peptide. Preferably linker A comprises a straight chain group, suitably of formula $-(CH_2)_a-$, wherein a is 1-20, preferably 1-15, 1-10, 1-5, or 2-4. Preferably linker A is covalently linked to spacer group X by an amide bond. Thus, in a preferred arrangement, linker A comprises the following general formula:

$$-NH-(CH_2)_a-NHCO-,$$

wherein a=1-20, preferably 1-15, 1-10, 1-5, or 2-4.

Preferably linker B does not include a disulphide bond. Preferably linker B (and the remainder of the non-peptide spacer) does not include more than one cyclic moiety. Preferably, linker B comprises a thioether bond. Such bonds are more stable than disulphide bonds.

The sealing member can be in the form of a patch, a powder, a paste, a gelatin, a spray, a foam, or a liquid. Suitable examples of sealing members include EviThrom Topical Human Thrombin, SURGIFLO® Hemostatic Matrix with Thrombin, Surgifoam® Absorbable Gelatin Sponge soaked with Thrombin, and SURGIFOAM® Absorbable Gelatin Powder mixed with Thrombin. Advantageously, the fibrinogen can be injected into the dural space prior to applying the sealing member, or the sealing member can be applied prior to injecting the fibrinogen into the dural space.

In one form, the dural tissue can be located between a patient's skull and lumbar portion of the spinal cord, such as below a patient's skull or in a patient's lumbar portion of the spinal cord.

Advantageously, the amount of fibrinogen injected into said dural space can be sufficient to raise a local volume concentration of fibrinogen in CSF fluid to at least about 0.75 mg/mL, such as from about 0.75 mg/mL to about 3 mg/mL. While higher concentrations can be used, little additional benefit is gained. The "local volume" can be from about 5 mL to about 20 mL within the dural space.

As illustrated in FIG. 2, the present disclosure is also directed to a kit for plugging a CSF leak site, comprising a syringe 100 containing a fibrinogen-containing solution and a patch 400 slidably disposed on a needle of said syringe, said patch containing a fibrinogen polymerizing agent. Inserting the syringe needle into the dural tissue 200 allows injection of the fibrinogen-containing solution into the dural space, and patch 400 is applied at that location to seal the defect made by the needle against CSF leakage.

In one form, the fibrinogen polymerizing agent can be selected from thrombin, thrombin with Factor XIII and thrombin-like enzymes, such as those present in snake venom, as described in more detail above.

In another form, the fibrinogen polymerizing agent can be a fibrinogen binding peptide or fibrinogen binding precursor peptide, as described in more detail above.

EXAMPLES

The following examples are illustrative of the principles and practice of the present disclosure, although not limited thereto.

A study was performed to assess the impact of different concentrations of fibrinogen useful in the presently disclosed method. The model utilized dura as the tissue substrate and the fluid under the dura was saline with different concentrations of fibrinogen. The defect was a 1 mm diameter punch in the dura and a Surgifoam® sponge lyophilized with thrombin was applied to the tissue and held for 5 minutes at 37° C. A control was tested without fibrinogen in the fluid under the tissue. Compared to the control without fibrinogen, the mean burst pressure was an order of magnitude higher for the fibrinogen-containing fluid, see the Table below. With fibrinogen levels as low as 0.75 mg/mL (25% of plasma) a substantial increase in burst pressure was observed. Plasma levels of fibrinogen (approx. 3 mg/mL) produced similar burst pressures.

TABLE

| Fibrinogen (mg/mL) | Sample size | Mean burst pressure (mm Hg) | Std. Deviation (mm Hg) | Minimum burst pressure (mm Hg) | Maximum burst pressure (mm Hg) |
|---|---|---|---|---|---|
| 0.00 | 10 | 7.3 | 4.4 | 0.9 | 15.7 |
| 0.75 | 10 | 71.1 | 43.7 | 22.7 | 154.0 |
| 1.50 | 10 | 90.2 | 83.1 | 33.3 | 308.6 |
| 3.00 | 10 | 75.3 | 38.9 | 28.3 | 166.6 |

Further illustrative, non-exclusive examples of methods and kits according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

PCT1. A method for stopping cerebrospinal fluid (CSF) leaks, comprising: penetrating and passing through a dural tissue an applicator to access an interior dural space; injecting from the applicator a fibrinogen-containing solution into said dural space; applying a sealing member containing a fibrinogen polymerizing agent onto an exterior surface of the dural tissue, and forming a polymerized fibrinogen or polymerized fibrin clot by contacting the injected fibrinogen-containing solution and the fibrinogen polymerizing agent.

PCT2. The method of paragraph PCT1, wherein the fibrinogen polymerizing agent is selected from thrombin, thrombin with Factor XIII and thrombin-like enzymes, such as those present in snake venom.

PCT3. The method of paragraph PCT1, wherein the fibrinogen polymerizing agent is a fibrinogen binding peptide or fibrinogen binding precursor peptide.

PCT4. The method of any preceding paragraph, wherein the sealing member is in the form of a patch, a powder, a paste, a gelatin, a spray, a foam, or a liquid.

PCT5. The method of any preceding paragraph, wherein the fibrinogen is injected into the dural space prior to applying the sealing member.

PCT6. The method of any preceding paragraph, wherein the sealing member is applied prior to injecting the fibrinogen into the dural space.

PCT7. The method of any preceding paragraph, wherein the dural tissue is located below a patient's skull.

PCT8. The method of any preceding paragraph, wherein the dural tissue is located in a patient's lumbar portion of the spinal cord.

PCT9. The method of any preceding paragraph, wherein the dural tissue is located between a patient's skull and lumbar portion of the spinal cord.

PCT10. The method of any preceding paragraph, wherein the amount of fibrinogen injected into said dural space is sufficient to raise a local volume concentration of fibrinogen in CSF fluid to at least about 0.75 mg/m L.

PCT11. The method of any preceding paragraph, wherein the amount of fibrinogen injected into said dural space is sufficient to raise a concentration of fibrinogen in a local volume of CSF fluid to at from about 0.75 mg/m L to about 3 mg/m L.

PCT12. The method of any preceding paragraph, wherein the fibrinogen containing solution is free of thrombin.

PCT13. The method of any preceding paragraph, wherein the fibrinogen is injected into the dural space in the vicinity of a defect in the dural tissue.

PCT14. A kit for plugging a CSF leak site, comprising: a syringe containing a fibrinogen-containing solution; and a patch slidably disposed on a needle of said syringe, said patch containing a fibrinogen polymerizing agent.

PCT15. The kit of paragraph PCT14, wherein the fibrinogen polymerizing agent is selected from thrombin, thrombin with Factor XIII and thrombin-like enzymes, such as those present in snake venom.

PCT16. The kit of paragraph PCT14, wherein the fibrinogen polymerizing agent is a fibrinogen binding peptide or fibrinogen binding precursor peptide.

INDUSTRIAL APPLICABILITY

The systems and methods disclosed herein are applicable to the medical device and health care industries.

It is believed that the disclosure set forth above encompasses multiple distinct embodiments with independent utility. While each of these have been disclosed in its preferred form, the specific embodiments thereof as disclosed and illustrated herein are not to be considered in a limiting sense as numerous variations are possible. The subject matter of the embodiments includes all novel and non-obvious combinations and sub-combinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and sub-combinations that are directed to one of the disclosed embodiments and are novel and non-obvious. Forms embodied in other combinations and sub-combinations of features, functions, elements and/or properties may be claimed through amendment of the present claims or presentation of new claims in this or a related application. Such amended or new claims, whether they are directed to a different embodiment or directed to the same embodiment, whether different, broader, narrower, or equal in scope to the original claims, are also regarded as included within the subject matter of the embodiments of the present disclosure.

What is claimed is:

1. A method for stopping cerebrospinal fluid (CSF) leaks, comprising:
   penetrating and passing through a dural tissue an applicator to access an interior dural space;
   injecting from the applicator a fibrinogen-containing solution into said dural space;
   applying a sealing member containing a fibrinogen polymerizing agent onto an exterior surface of the dural tissue, and
   forming a polymerized fibrinogen or polymerized fibrin clot by contacting the injected fibrinogen-containing solution and the fibrinogen polymerizing agent.

2. The method of claim 1, wherein the fibrinogen polymerizing agent is selected from thrombin, thrombin with Factor XIII, Batroxobin, Ancrod and Venzyme.

3. The method of claim 1, wherein the fibrinogen polymerizing agent is a fibrinogen binding peptide or fibrinogen binding precursor peptide.

4. The method of claim 1, wherein the sealing member is in the form of a patch, a powder, a paste, a gelatin, a spray, a foam, or a liquid.

5. The method of claim 1, wherein the fibrinogen-containing solution is injected into the dural space prior to applying the sealing member.

6. The method of claim 1, wherein the sealing member is applied prior to injecting the fibrinogen-containing solution into the dural space.

7. The method of claim 1, wherein the dural tissue is located below a patient's skull.

8. The method of claim 1, wherein the dural tissue is located in a patient's lumbar portion of the spinal cord.

9. The method of claim 1, wherein the dural tissue is located between a patient's skull and lumbar portion of the spinal cord.

10. The method of claim 1, wherein the amount of fibrinogen-containing solution injected into said dural space is sufficient to raise a local volume concentration of fibrinogen in CSF fluid to at least about 0.75 mg/mL.

11. The method of claim 1, wherein the amount of fibrinogen-containing solution injected into said dural space is sufficient to raise a concentration of fibrinogen in a local volume of CSF fluid to at from about 0.75 mg/mL to about 3 mg/mL.

12. The method of claim 1, wherein the fibrinogen-containing solution is free of thrombin.

13. The method of claim 1, wherein the fibrinogen-containing solution is injected into the dural space in the vicinity of a defect in the dural tissue.

\* \* \* \* \*